United States Patent [19]
Gordon et al.

[11] Patent Number: 5,768,331
[45] Date of Patent: Jun. 16, 1998

[54] X-RAY TOMOGRAPHY SYSTEM FOR AND METHOD OF IMPROVING THE QUALITY OF A SCANNED IMAGE

[75] Inventors: Bernard M. Gordon, Magnolia; John Dobbs, Hamilton; David Banks, Boxford, all of Mass.

[73] Assignee: Analogic Corporation, Peabody, Mass.

[21] Appl. No.: 653,113

[22] Filed: May 24, 1996

Related U.S. Application Data

[63] Continuation of Ser. No. 191,428, Feb. 3, 1994, abandoned.
[51] Int. Cl.⁶ .................................................. H05G 1/60
[52] U.S. Cl. .................................................. 378/19; 378/4
[58] Field of Search ........................... 378/19, 11, 4

[56] References Cited

U.S. PATENT DOCUMENTS

| | | | |
|---|---|---|---|
| 4,048,505 | 9/1977 | Hounsfield | 378/19 |
| 4,176,279 | 11/1979 | Schwiery et al. | 378/19 |
| 4,689,809 | 8/1987 | Sohval | 378/136 |
| 4,819,260 | 4/1989 | Haberrecker | 378/137 |
| 4,841,553 | 6/1989 | Nagai | 378/19 |
| 4,894,850 | 1/1990 | Frings et al. | 378/62 |
| 5,065,420 | 11/1991 | Levene | 378/137 |
| 5,259,014 | 11/1993 | Brettschneider | 378/138 |
| 5,550,886 | 8/1996 | Dobbs et al. | 378/19 |

*Primary Examiner*—Craig E. Church
*Attorney, Agent, or Firm*—Lappin & Kusmer LLP

[57] ABSTRACT

A scanning tomography system has a gantry including a disk for supporting a X-ray source and detector array and rotatable about a central axis. Multiple scans are made to reduce the effects of motion artifacts and improve image quality. In addition, the detector array is supported by a suspension system and is movable about the focal spot of the X-ray source a small amount so that in one mode of operation the detector array can be shifted at a predetermined angle from one position to at least one other position during a scan so as to provide an increase in the number of unique X-ray paths so as to provide improved image quality. In a second mode of operation, the detector array can be offset from the center ray so as to provide a quarter of a detector offset.

35 Claims, 6 Drawing Sheets

X-RAY TOMOGRAPHY SYSTEM FOR AND METHOD OF IMPROVING THE QUALITY OF A SCANNED IMAGE

RELATED APPLICATIONS

This application is a continuation of U.S. patent application Ser. No. 08/191,428 filed Feb. 3, 1994, now abandoned, and is related to co-pending U.S. patent application Ser. No. 08/190,945, filed in the names of John Dobbs and David Banks contemporaneously herewith and assigned to the present assignee (Attorney's Docket No. ANA-23); and U.S. patent application Ser. No. 08/191,426, filed in the names of John Dobbs; David Banks and Leonhard Katz contemporaneously herewith and assigned to the present assignee (Attorney's Docket No. ANA-47).

FIELD OF THE INVENTION

This invention relates generally to computer assisted tomography (CAT), and more particularly to improvements in the quality of a CAT scan image.

BACKGROUND OF THE INVENTION

CAT scanners of the third generation type include an X-ray source and X-ray detector system secured respectively on diametrically opposite sides of an annular-shaped disk. The latter is rotatably mounted within a gantry support so that during a scan the disk continuously rotates about a rotation axis while X-rays pass from the source through an object positioned within the opening of the disk to the detector system.

The detector system typically includes an array of detectors disposed as a single row in the shape of an arc of a circle having a center of curvature at the point, referred to as the "focal spot," where the radiation emanates from the X-ray source. The X-ray source and array of detectors are all positioned so that the X-ray paths between the source and each detector all lie in the same plane (hereinafter the "slice plane" or "scanning plane") normal to the rotation axis of the disk. Because the ray paths originate from substantially a point source and extend at different angles to the detectors, the ray paths resemble a fan, and thus the term "fan" beam is frequently used to describe all of the ray paths at any one instant of time. The X-rays that are detected by a single detector at a measuring instant during a scan is considered a "ray." The ray is partially attenuated by all the mass in its path so as to generate a single intensity measurement as a function of the attenuation, and thus the density of the mass in that path. Projection views, i.e., the X-ray intensity measurements, are typically done at each of a plurality of angular positions of the disk.

An image reconstructed from data acquired at all of the projection angles during the scan will be a slice along the scanning plane through the object being scanned. In order to "reconstruct" or "back project" a density image of the section or "slice" of the object in the defined scanning plane, the image is typically reconstructed in a pixel array, wherein each pixel in the array is attributed a value representative of the attenuation of all of the rays that pass through its corresponding position in the scanning plane during a scan. As the source and detectors rotate around the object, rays penetrate the object from different directions, or projection angles, passing through different combinations of pixel locations. The density distribution of the object in the slice plane is mathematically generated from these measurements, and the brightness value of each pixel is set to represent that distribution. The result is an array of pixels of differing values which represents a density image of the slice plane.

In order for the image reconstruction process to work, however, the ray sums must be assigned to the proper pixels, i.e., each pixel that lies in the path traversed by the individual respective ray. When ray sums are assigned to improper pixels, not only are the density values of the affected pixels in error, but, because of the Radon algorithm, artifacts in the form of rings and other geometric patterns can appear in the image and tend to obscure it.

Since a typical scan involves over a hundred million ray sums, in order to accurately map the ray paths through the pixel field without an unmanageable amount of calibration work, it is very useful to be able to assume very uniform and accurately located detectors and measurements timed to occur at precise rotation intervals, e.g., exactly equivalent to the spacing between detectors in the array. Co-pending patent application, U.S. Ser. No. 08/190,945 entitled "Modular Detector Arrangement for X-ray Tomographic Scanner," filed simultaneously herewith in the name of John Dobbs and David Banks and assigned to the present assignee (Attorney's Docket No. ANA-23), describes and claims a modular arrangement for very accurately locating and aligning detectors on a support spine. In order for the detectors to be accurately positioned and aligned with respect to the X-ray source and the patient object, however, there is a need for a readily adjustable mounting system to mount the spine to the rotating gantry.

In addition to inaccurate detector placement, incorrect assignment of rays to pixels can be caused by even slight patient object movement during the scan. It is very advantageous therefore, to be able to complete the scan within a few seconds, so that the patient can remain still during a scan, and if necessary hold his or her breath.

While such faster scans can help reduce motion artifacts, certain scans require a minimum exposure (for example, a typical brain scan requires a typical X-ray source to receive a total of 300–400 milliamp-seconds to provide sufficient X-ray exposure), and with faster scans at the same X-ray exposure level, the number of photons received by each detector will necessarily decrease because of the shorter exposure time. Thus, shortening the time of the scan necessarily means that the tube must be operated at a higher level in order to provide a sufficient number of photons to complete the scan. Where the power source available is insufficient to deliver high rates of power, the conventional wisdom is that the scan must be slowed down sufficiently so that an adequate number of photons are provided during the 360° rotation to provide sufficient image data for the scan. This, of course, increases the errors attributed to motion artifacts. If the patient moves during the scan the data taken during the latter part of the scan will be inconsistent with that taken earlier. The magnitude of the artifact will be related to the magnitude of the motion.

One solution is to provide a high speed, multiple scan, without substantially increasing the overall scanning time nor the X-ray exposure level. Thus, for example, by halving the time of a typical 360° scan, e.g., a 4-second scan, and repeating the scan to duplicate the data, i.e., performing two successive 2-second, 360° scans, and summing the duplicated data from the two scans so as to superimpose two scan images, errors due to motion artifacts can be reduced. Thus, if a patient only moves during the first 2-second scan, the second scan will free of motion artifacts. Summing the two scans results in the summation of a 2-second scan with an artifact with an 2-second artifact free scan. If the patient moves continuously during the entire 4 seconds, then the magnitude of the artifact will be smaller in each of the 2-second scans than it would be in the slower 4-second scan so that the summed picture will contain two small artifacts instead of one larger artifact. Since artifact creation is very non-linear, small motions have a disproportionately smaller effect on the image quality than large motions.

Another parameter affecting image quality is related to the total number of unique ray paths of a scan. In general, the larger the number of unique ray paths of a scan that can be assigned to the proper image pixels, the better the resulting image. To obtain the benefit of increasing the number of unique ray paths that can be assigned to the image pixels of the reconstructed image, it is well known to mount the detector array relative to the source and rotation center of the disk, i.e., the "isocenter", so that ray placement is offset by a fixed one-quarter of the spacing of the detector. The offset is referenced to the center line passing from the focal spot of the source through the isocenter to a detector of the array. Thus, without an offset the center ray is aligned with the center of the detector. With a fixed quarter of a detector offset the center ray is offset a fixed quarter of the spacing of the detector from the center of the detector. With such a fixed offset, during a second 180° scan all of the detectors will be displaced by one-half of the detector-spacing from the detector placement during the first 180° of the scan. This, therefore, doubles the number of unique ray paths for a 360° rotation scan from the centered arrangement, without generating redundant information.

Figure 1:
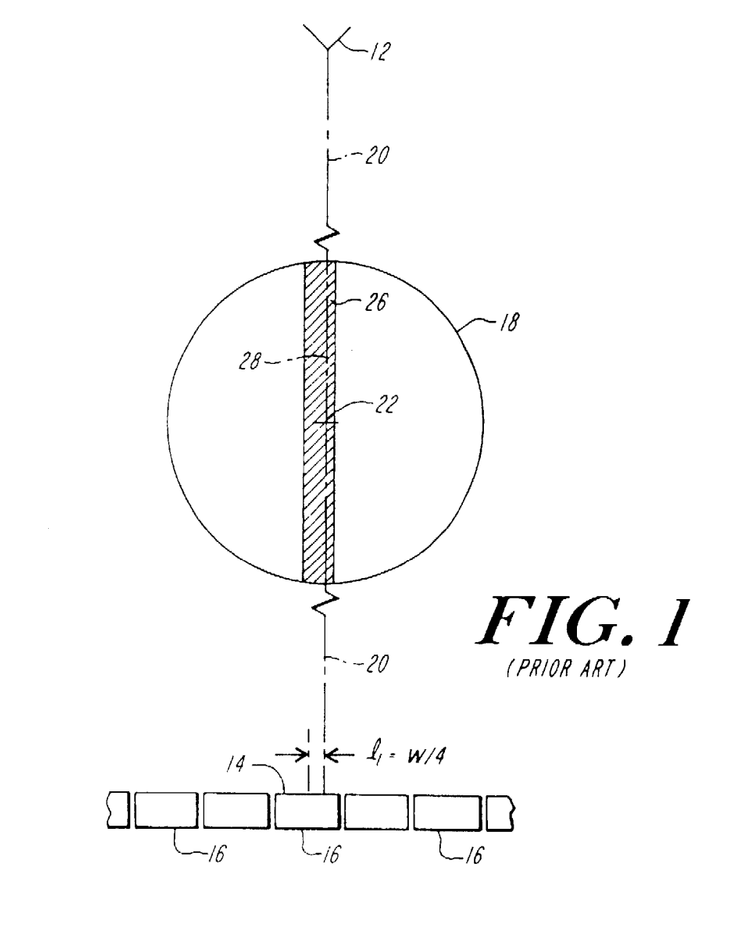
FIGS. 1 and 2 are diagrams illustrating the effect of a detector array offset according to the prior art.
Figure 2:
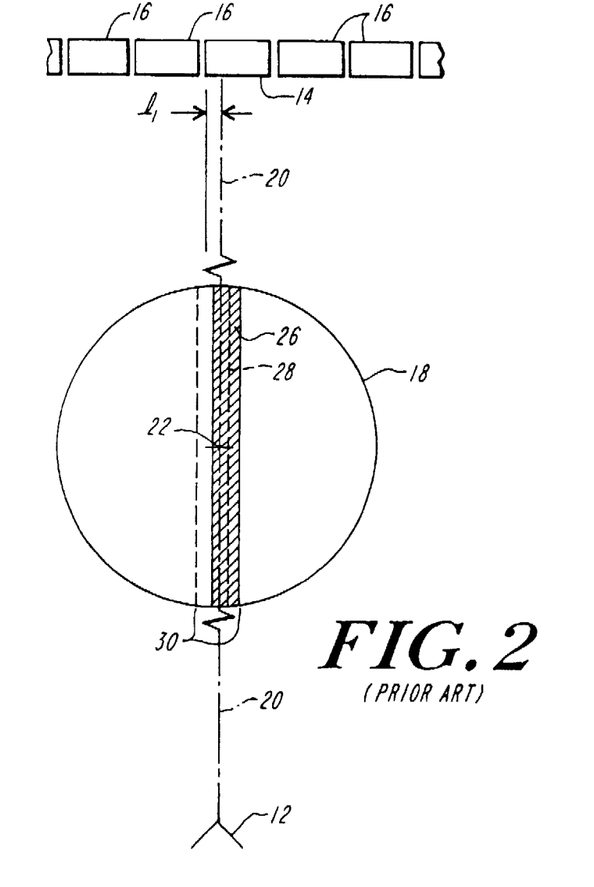
Figure 3:
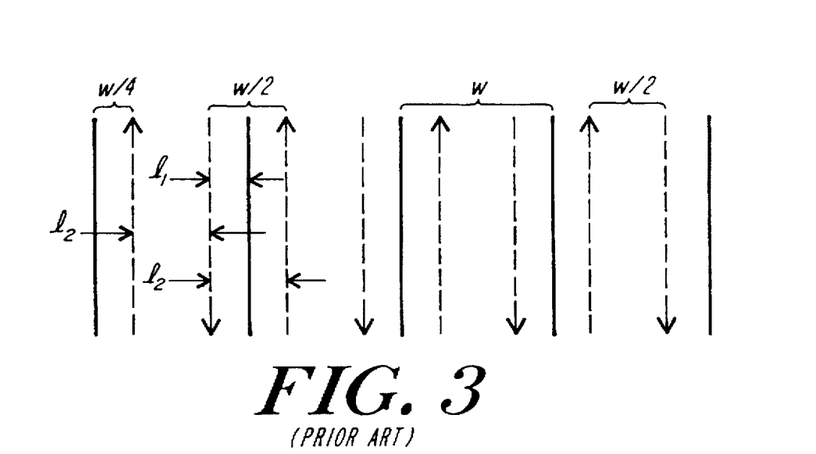
FIG. 3 is a schematic diagram illustrating ray placement of the rays for the two projection views shown in FIGS. 1 and 2 which are diametrically opposite one another.

For an illustrative explanation of this prior art scheme reference is made to FIGS. 1–3. FIGS. 1 and 2 depict the focal spot of the X-ray source 12, a particular detector 14 within the array of detectors 16 of a scanning tomography system and a portion 18 of the patient object disposed between the source and detectors, portion 18 being referred to as the measurement field. FIG. 1 shows an instant when the X-ray source 12 is at the top and detector 14 is at the bottom. FIG. 2 represents an instant 180 degrees later in the same scan, when detector 14 is at the top and source 12 is at the bottom. Dot-dash line 20, which passes between source 12 and detector 14, also passes through isocenter or rotation center 22. The latter is the center of rotation, or where the rotation axis of the rotating disk supporting the source 12 and detector array 16 intersects the scanning plane of the system. Line 20 is broken in two places to indicate that, while detector 14 and object portion 18 are drawn to the same approximate scale, the distances between them and the source have had to be greatly shortened for ease of illustration.

A ray has already been defined as that portion of the X-ray beam that is detected by a single detector. Since the rays detected by detector 14 always pass through the rotation center 22, they may be termed "central rays". Cross-hatched area 26 in each figure shows the area in the object portion 18 which has been exposed by the central ray at each of the two positions shown. Since the detectors are offset by an amount $l_1$ equal to one-quarter the spacing of a detector (w/4) the center 28 of the central ray exposing the area 24 and detected by detector 14 (the center of the ray is drawn from source 12 to the center of detector 14) does not extend through the center 22 but is displaced to the left in FIG. 1 by an amount proportional to one-quarter the spacing of the detector, and is displaced to the right in FIG. 2 by an amount proportional to one-quarter the spacing of the detector. Thus, referring to FIG. 3, the center line 28 of the ray 20 as seen in FIGS. 1 and 2 is offset in the two figures by an amount $l_2$ equal to one-half of the ray spacing (w/2) so that ray placement for the detectors at the position shown in FIG. 2 which occurs during the second 180° (shown as dashed arrows pointing up) will be precisely between the ray placement for the detectors at the diametrically opposite position shown in FIG. 1 which occurs during the first 180° scan (shown as dashed arrows pointing down). As a result, the area of object portion 18 penetrated by the central ray at the measuring instant of FIG. 2, as indicated by cross-hatched area 26, is displaced by an amount proportional to one-half the spacing of the detector as indicated at 30 in FIG. 2 from that penetrated during the measuring instant of FIG. 1. The same is true of all the rays for the 360° of rotation. As a result, the measurement data from the second 180 degrees of the scan represents samples taken at intervals half-way between those of the first 180 degrees. This doubles the number of unique ray paths and greatly contributes to clarity of the reconstructed image. In a modern practical system where there may be, for example, eight detectors to a degree of rotation, and detectors are centered approximately 1.8 millimeters apart, this offset represents only 1/32 of a degree and less than about 0.05 mm.

OBJECTS OF THE INVENTION

Accordingly, one object of the present invention is to reduce the effects of motion artifacts on tomography imaging without increasing the X-ray exposure to a patient during a scan.

Another object of the present invention is to provide an improved X-ray tomographic scan having the benefit of a longer scan from the point of view of quantum statistics without actually increasing the scanning time, nor the X-ray exposure level.

And another object of the present invention is to provide an improved tomographic scan which can be accomplished where the power source available is insufficient to deliver high rates of power.

Yet another object of the present invention to generally improve the image quality of a reconstructed image provided by a CAT scan system of the type having an array of detectors offset by a fixed quarter of the spacing of each detector.

Still another object of the present invention is to provide an improved tomography system providing additional unique ray paths from those provided by the prior art system using a standard one-quarter detector-spacing offset.

And yet another object of the present invention is to provide an improved mounting system for supporting an array of detectors in a tomography system so as to provide precise detector placement relative to the X-ray source and isocenter and sufficiently rugged to sustain high angular acceleration forces, and yet adapted to rotate the detector array at least through a small angle about the focal spot between at least two precisely defined positions.

And still another object of the present invention is to provide such an improved mounting system for supporting an array of detectors in a tomography system wherein the precise detector placement is easily adjustable through an input device, such as a keyboard, making it easier to ship the tomography system, set the system up during installation and calibrate the detector placement as necessary on an on-going basis.

And yet another object of the present invention is to provide an improved tomography system capable of operation in either of at least two modes for defining scans for two different quality images.

SUMMARY OF THE INVENTION

The foregoing objects are achieved by an improved detector support system which includes means for moving the detector array relative to a line passing through the focal spot and isocenter, between at least two positions. The detectors can be moved between scans and/or during a scan. Detector movement preferably is provided so as to increase the number of unique ray paths during a scan. For example, the preferred embodiment described hereinafter in connection with the drawings is designed for a multiple scan comprising two 360° scans. The two positions are defined to provide a one-eighth detector-spacing placement for the first 360° scan and a three-eighths detector-spacing placement for the second 360° scan, although the detector-spacing placements selected for each position can vary, as described in greater detail hereinafter. The image data from both scans are combined so as to provide improved image quality of the reconstructed image from that produced by the one-quarter detector-spacing offset during a single 360° scan. In the preferred system, the detector array can also be moved to a one-quarter detector-spacing offset to provide a second operating mode. The mounting system for securing the detector array to the tomography system is preferably a suspension system, such as a four bar suspension system, for allowing the detector array to move relative to the radiation source to approximate rotation about the focal spot over a small angle equal to the one-quarter detector-spacing movement, or other angles depending on the design of the CAT scan system.

These and other objects of the invention will in part be apparent and will in part appear hereinafter. The invention accordingly comprises the apparatus possessing the construction, combination of elements, and arrangement of parts, and the processes involving the several steps and the relation and order of one or more of such steps with respect to the others, all of which are exemplified in the following detailed disclosure and the scope of the application all of which will be indicated in the claims.

DETAILED DESCRIPTION OF THE DRAWING

Figure 4:
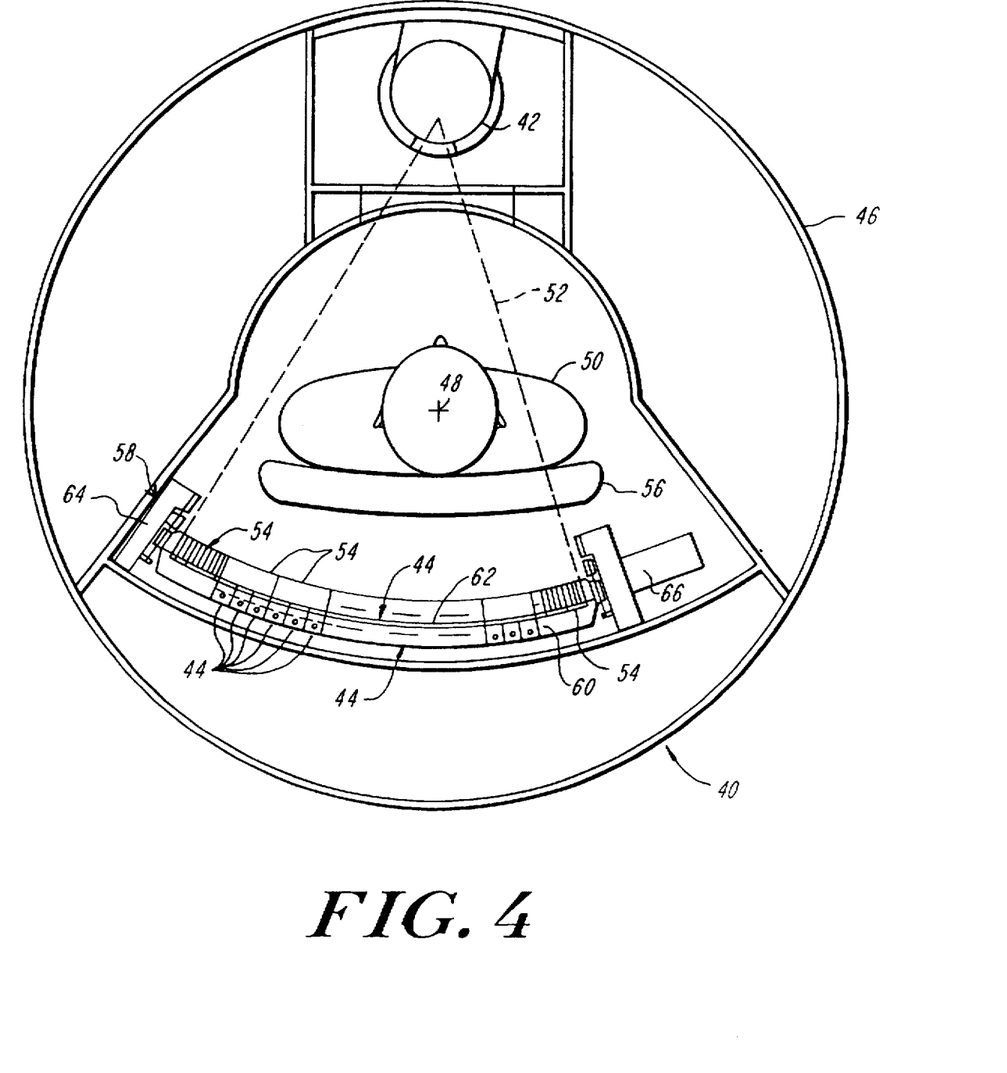
FIG. 4 is an axial view of a CAT scanner embodying the preferred arrangement of the present invention.

For a more complete understanding of the invention reference is made first to FIG. 4, which represents a tomography scanner 40 incorporating the principles of the present invention. To provide the data for a CAT scan, scanner 40 includes a source 42 of X-rays and detector assembly 44 comprising an array of detectors and mounted to a disk 46. Source 42 and detector assembly 44 are rotated about rotation axis 48 (extending normal to the view shown in FIG. 4) so as to rotate around the object 50 that extends through the central opening of the disk during the CAT scan. Object 50 may be a part of a live human patient, such as the head or torso. Source 42 emits within the scanning plane (normal to rotation axis 48) a continuous fan-shaped beam 52 of X-rays, which are sensed by the detectors of assembly 44 after passing through object 50. An array of anti-scatter plates 54 is located between object 50 and the detectors of assembly 44 to substantially prevent scattered rays from being sensed by the detectors. In the preferred embodiment the detectors number 384 and cover an arc of 48°, although the number and angle can vary. Disk 46, which may advantageously be of a light weight material, such as aluminum, is caused to rotate rapidly and smoothly around axis 48. The disk 46 is of an open frame construction so that object 50 can be positioned through the opening of the disk. Object 50 may be supported, for example, on a table 56, which of course, should be as transparent as practical to X-rays. As disk 46 rotates, the detectors of assembly 44 are periodically sampled to provide discrete measurements of X-rays passing in the scanning plane through object 50 from many projection angles. The measurements, representing image data, are then processed electronically with appropriate signal processing equipment (not shown), in accordance with well-known mathematical techniques, so as to produce the final image information. The image information may then be placed in memory, analyzed in a computer, or suitably displayed.

If a typical scan of one 360° revolution is performed at a predetermined time interval at a preselected X-ray exposure level, better results can be achieved by performing the scan so that it comprises two or more consecutive 360° scan revolutions, described herein as a "multiple scan", during substantially the same time interval and at the same X-ray exposure level. The image data from each of the 360° scan revolutions is summed with the corresponding image data from the other 360° scan revolutions so that the effect of motion artifacts occurring during the multiple scan on the final image is reduced. With the detector array mounted relative to the source so that the array is fixed throughout the entire scan, e.g., the center line or ray passing through the focal spot and the isocenter of the rotatable disk is aligned with the center of a detector of the array with all of the detectors subtending the same angle relative to the focal spot of the source, the scan will essentially repeat itself every 360° and the data acquired during each 360° scan should duplicate the image data acquired. Thus, by shortening the time period of each revolution of the multiple scan, there is a greater chance that the patient will move less within each shorter period of one 360° of rotation, and by providing at least a second set of data from the second 360° of rotation, and adding the second set of data to the first set of data, will reduce the effect of the errors due to the artifacts. Yet the total X-ray flux passing through the patient during the measurement period will not appreciably change. Thus, by summing the data from the all of the revolutions of the multiple scan, one will reduce the effects of the patient movement, without appreciably increasing the patient's exposure to X-rays.

As an example, if a typical single 360° revolution scan is performed during a 4 second interval, the data taken during the final projection view at the end of the scan must be reconciled with the very first projection view at the beginning of the scan. This reconciliation will fail to the extent the patient moves during the 4 second interval. By taking a two revolution multiple scan, i.e., taking data during two 360° consecutive revolutions at the same exposure level and over the same 4 second interval (at twice the rotational speed), the final projection view at the end of the first revolution must be reconciled with the first projection view at the beginning of the revolution but, will fail to the extent that the patient moves during only a 2 second interval. A similar reconciliation must be made during the second revolution, but again will only suffer from the patient's movement during a 2 second interval. The data from the first revolution is summed with the data from the second revolution so as to provide data from a 4 second multiple scan at the same exposure level as the single revolution 4 second scan, thus accomplishing the multiple scan without increasing the level of X-rays to which the patient is exposed.

In accordance with the present invention, in order to improve image quality, the detector assembly 44 is mounted on the disk so as to be precisely positioned relative to the source 42 and the rotation axis 48, but movable through a small rotation angle about a central point coincident with the focal spot of the source 42 between at least two positions so that the number of unique ray paths provided during a multiple scan can be increased from that provided with a fixed one-quarter detector-spacing offset. In this case the data collected during the second revolution does not duplicate the data collected during the first revolution of the scan because of the different ray paths during the second revolution. The ray paths of the second revolution are interleaved with the ray paths of the first revolution so as to provide an improved quality reconstructed image.

An embodiment of the suspension system of the invention which facilitates the desired precision adjustment of the detector array while possessing the desired ruggedness is further illustrated in FIGS. 5–11. The illustrated mounting system 58 preferably includes a detector and antiscatter plate support spine 60 which supports the detector assembly 44 and antiscatter plates 54 along an arcuate line 62 (seen in FIG. 4, and schematically illustrated in FIGS. 10 and 11) which has its center of curvature at the focal spot (indicated at point 124 of FIG. 10) of source 42 such that each detector subtends an equal angle about that center. Mounting system also includes two post supports 64, each of which attaches to disk 46 and to a respective end of spine 60. A reversible stepping motor 66, which may be attached to one of supports 64. The stepping motor can provide very small precise movements with each step and therefore can provide an automatic detector array angular position adjustment, as described in greater detail hereinafter. By keeping track of the number of steps one can determine at any one instant of time the precise position of the detector array and therefore provide the precise positioning of the detector array in accordance with the principles of the present invention.

Figure 5:
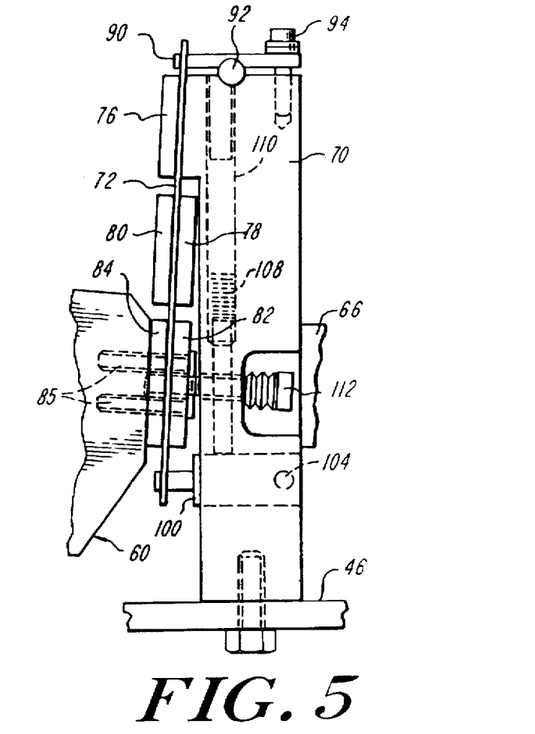
FIG. 5 is an axial view of the post support for attaching the spine of the mounting system to the rotating disk.
Figure 8:
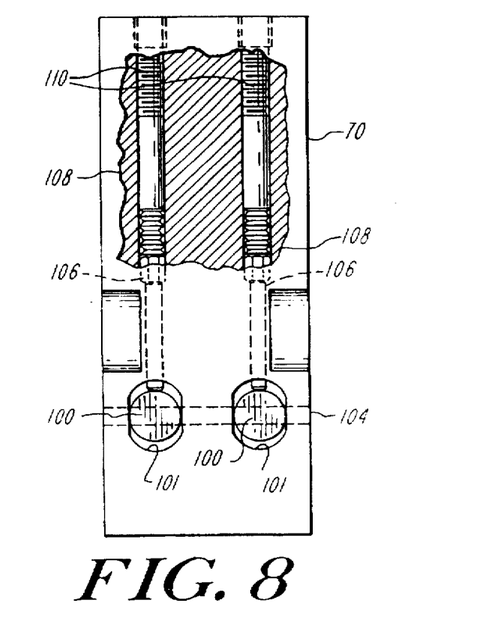
FIG. 8 is a partial, tangential view (opposite to that shown in FIG. 6) of the post support shown in FIGS. 5–7.
Figure 9:
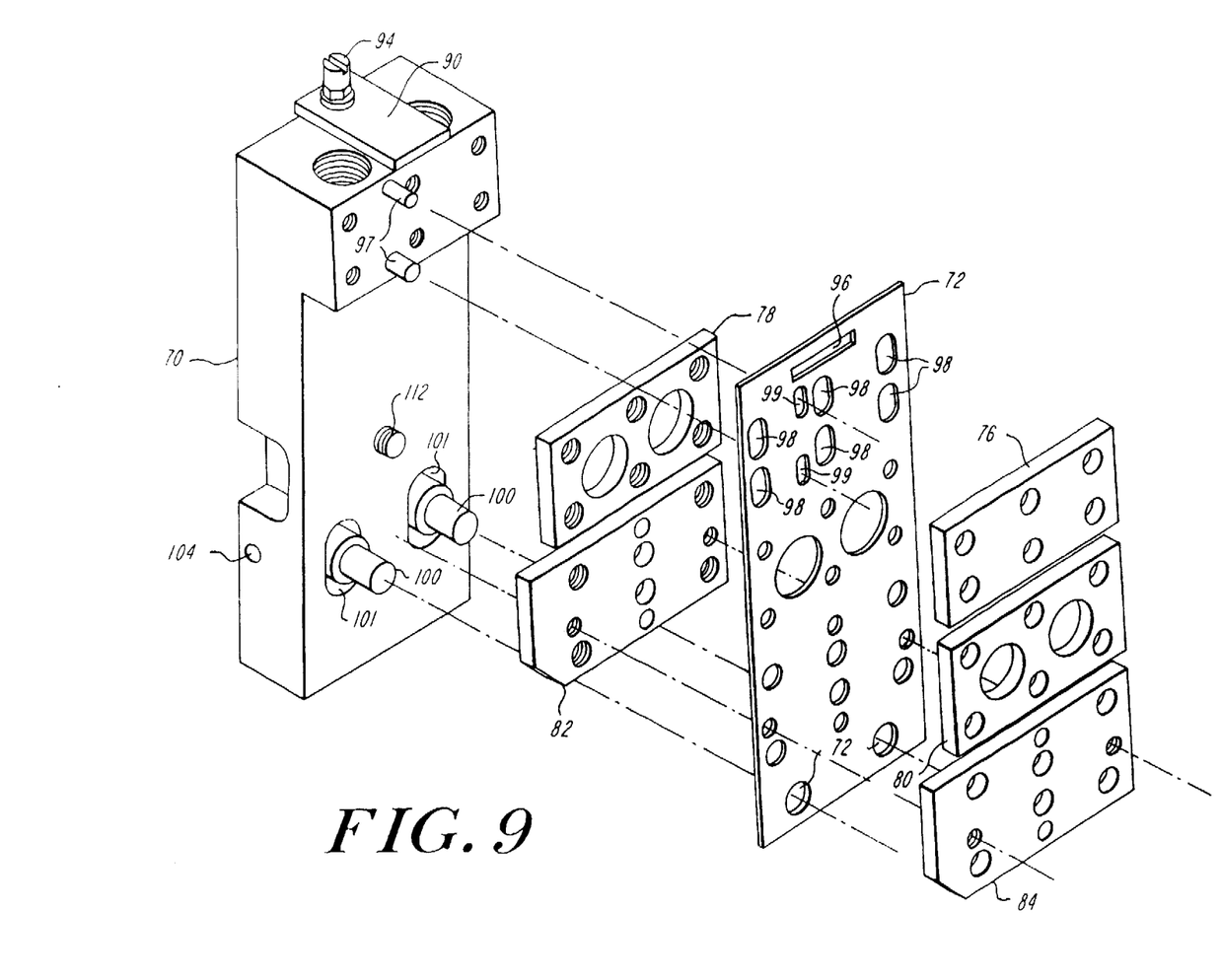
FIG. 9 is an exploded perspective view of the preferred suspension system of the present invention.

A suitable arrangement for attaching the post supports 64 to respective ends of spine 60 and to disk 46 is shown in FIGS. 5–8, and the partially exploded assembly drawing of FIG. 9. The end of support 64 nearest the X-ray source 42 is shown as the top in these drawings. The major components of a support 64 are a support body 70, which as seen in FIG. 5 bolts to disk 46, a thin, flexible mounting plate 72, which respectively bolts at opposite ends to body 70 and spine 60. The plate 72 is preferably made of a material having high flexibility and strength, such as stainless steel.

Figure 6:
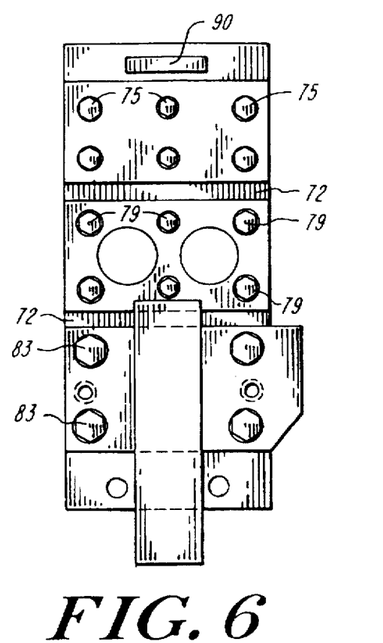
FIG. 6 is a tangential view of the post support shown in FIG. 5.
Figure 7:
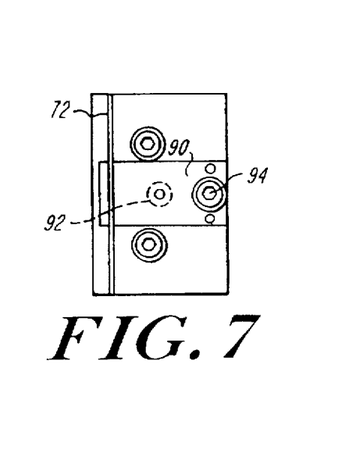
FIG. 7 is a radial view of the post support shown in FIGS. 5 and 6.

For reasons which will be more clearly described hereinafter, flexible plate 72 is sandwiched between three pairs of rigid surfaces, five of which are on separate stiffeners 76, 78, 80, 82 and 84. As best seen in FIG. 6, a first stiffener 76 holds the upper section of plate 72 against body 70 by bolts 75 or the like. A pair of stiffeners 78 and 80 may be applied to opposite sides of the middle section of plate 72 by bolts 79 through stiffener 78 and plate 72 into stiffener 80. Similarly, a pair of stiffeners 82 and 84 may be secured to opposite sides of a lower section of plate 72 by bolts 83. As best seen in FIGS. 5 and 6 additional bolts 85 through the center of stiffeners 82 and 84 and plate 72 into threaded holes in the end of spine 60 securely fasten the spine 60 to stiffening member 84, and thus to post support 64.

As best seen in FIGS. 5 and 9, fine adjustment of the position of spine 60 in the radial direction, toward and away from the source 42, to assure that all detectors are the same distance from the focal spot, may be provided by a lever 90, a pivot ball 92, a screw 94, located at the top of each support 70. One end of lever 90 protrudes through a rectangular hole 96 (see FIG. 9) in plate 72. Screw 94 extends through lever 90 at the other end and is threaded into the top of body 70. Ball 92, partly recessed into body 70 and into lever 90, serves as a fulcrum so that as screw 94 is driven into body 70, plate 72 is raised, and vice versa. The elongated holes 98 in plate 72 through which bolts 75 extend accommodate this adjustment, which is made before stiffener 76 is firmly secured. A pair of dowel pins 97, in body 70, and associated slots 99 in plate 72 and stiffener 76, assure radial alignment wherein the width of each slot is dimensioned to tightly receive the corresponding pin.

Plate 72 may be kept under constant tension to avoid movement when subjected to operating forces by a pair of tensioning levers 100, which protrude through slots 101 provided in body 70, and into holes 102 in plate 72. Both levers 100 pivot up and down in slots 101 on a common pivot rod 104, that passes through body 70 and levers 100. As best seen in FIG. 8, driving each of tensioning levers 100 may be a push rod 106, an appropriate stack of compression (belleville) washers 108 and a tensioning screw 110. The compression washers maintain a constant pressure on push rods 106 and therefore constant tension on plate 72 over a limited range of movement. The size washer is chosen according to the amount of tension desired, and the number of washers in the stack is chosen to accommodate the range of movement desired for final adjustment.

In order to effect movement of the spine the motor 66 rotates a screw 112 (seen in FIGS. 5 and 9) against stiffener member 84. Thus, operating the motor in one direction moves the screw against the stiffener and thus against the tension provided by the flexible plates 72 so as to effect movement of the spine in one direction. Operating the motor in the opposite direction allows the screw to move away from the stiffening member 84 so that the spine moves in the opposite direction due to the tension provided by the flexible plates.

The fine precision movement for moving the detector array will now be described in greater detail. While it is possible to practice the invention without them, stiffeners 76, 78, 80, 82 and 84 serve a very useful purpose in this context. They limit the bending of flexible plate 72 to two narrow, unsupported areas, which span the width of the plate, closely simulating two hinges. Since the detector array is hung from two such restrained plates, it is essentially supported on four hinges, in what is commonly termed a four-bar suspension system. An understanding of the operation of this arrangement and its advantages may be aided by reference to FIGS. 10 and 11.

Figure 10:
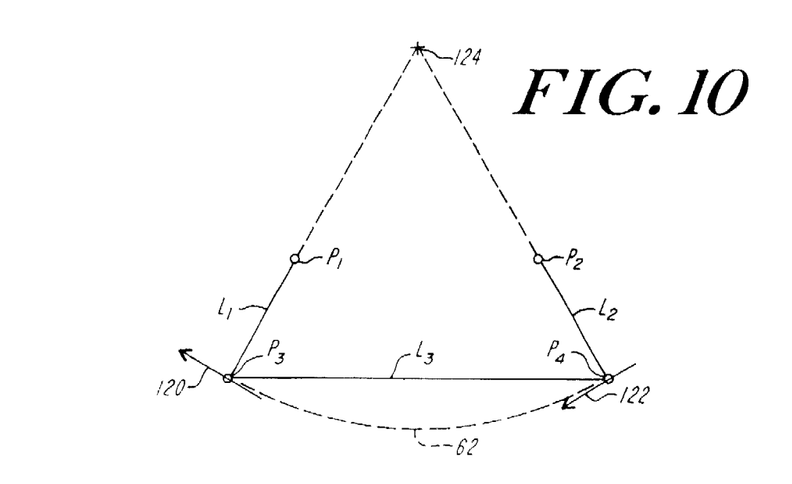
FIGS. 10 and 11 are a diagram and a pictorial view, respectively, illustrating the spatial adjustment of the detector array in accordance with the present invention.

FIG. 10 diagrammatically illustrates a four-bar suspension system, similar to that provided by the two supports 64 and spine 60. Two pivot points, $P_1$ and $P_2$, are fixed; the other two, $P_3$ and $P_4$, are movable. Rigid beams $L_1$, $L_2$ and $L_3$ connect $P_1$ and $P_3$, $P_2$ and $P_4$ and $P_3$ and $P_4$, respectively. $P_3$ is restricted to move along a portion of a circle with $P_1$ as its center, and $P_4$ is restricted to move along a portion of a circle with $P_2$ as its center. Since beam $L_3$ joins them, $P_3$ and $P_4$ must move together in the same sense, clockwise or counterclockwise. When $P_3$ goes up to the left therefore, as shown by arrow 120, $P_4$ goes down to the left, as shown by arrow 122. Arrow 120 is tangent not only to a circle about point $P_1$, but to every circle whose center is on the straight line defined by $P_1$ and $P_3$. Similarly, arrow 120, which defines the movement of the right side of the four-bar system, is tangent to every circle whose center is on the line defined by $P_2$ and $P_4$. For small distances, therefore, the movement of beam $L_3$ is a very close approximation to rotation about the point 124, which is common to both lines, i.e., where $L_1$ extended intersects $L_2$ extended, shown by dotted lines.

Figure 11:
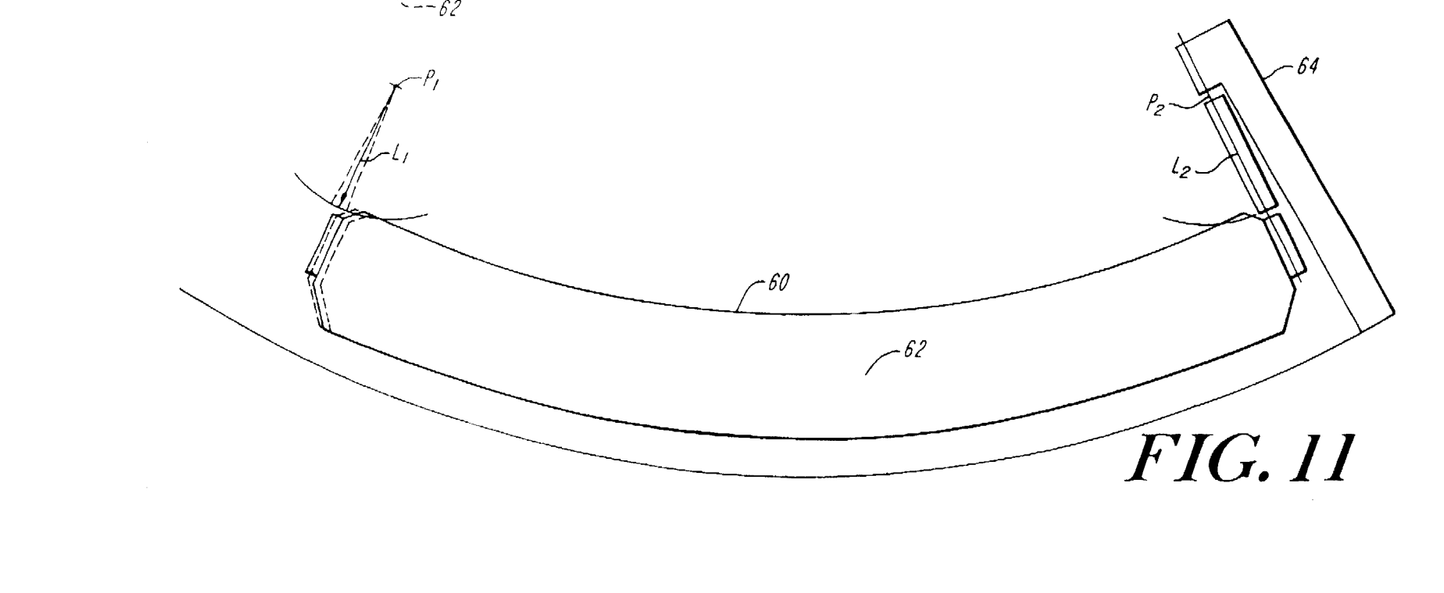

Moving from the diagram of FIG. 10 to the sketch of FIG. 11, points $P_1$ and $P_2$ correspond approximately to those points between adjacent stiffeners. $L_1$ and $L_2$ correspond to the mid-sections stiffened by stiffeners 78 and 80. Point 124 corresponds to the position of the focal spot of the X-ray source 42. When the position of spine 60 is changed by adjustment screw 112 (as determined by stepping motor 66), therefore, the whole detector array moves the small distance along the arc that has the focal spot as its center. Since the detectors are mounted on spine 60 along arcuate line 62 with its center at the focal spot, the adjustment merely rotates the array without changing the distance between the source and any detector and thus each detector will still subtend an equal angle. It should be noted here, that while stiffeners 76, 78, 80 82 and 84 provide some advantage, the system still approximates a four-bar suspension without them. Similarly, it will be understood that a pair of suitable hinges could be substituted for each plate 72, where the latter attaches to the disk and to the spine to practice the invention.

Preferably, the detector array can be shifted between a position where the detector array is offset n/8 of the spacing of a detector, where n is an odd integer 1, 3, 5 or 7 during a 360° rotation of a two revolution scan, and offset n/8±¼ of the spacing of a detector during the second 360° rotation of the two revolution scan. For example, the array can be shifted between a position where the detector array is offset ⅛th of the spacing of a detector (w/8), and offset ⅜ths of the spacing of a detector during the second 360° rotation of the two revolution scan. In the example, the sequence can be either providing the one-eighth detector-spacing offset set during the first 360° or during the second 360° rotation with the same results. The shift occurs precisely when the first 360° of the scan has occurred. Because of the time necessary to effect the shift, the disk 46 will actually rotate a predetermined amount before the detectors are set to provide image data for the second 360° revolution of the two revolution scan. The actual amount of rotation of the disk between the two revolutions of the disk when image data is acquired, is a function of the rotational speed of the disk and the response time of the detector support and shifting mechanisms. If, for example, the detectors provide data for a first 360° rotation of a multiple scan, and during the shift of the detectors (when no data is acquired) the disk rotates 40°, the detectors will begin providing data for the next 360° rotation so that the disk actually rotates 760° for a two revolution multiple scan.

Figure 12:
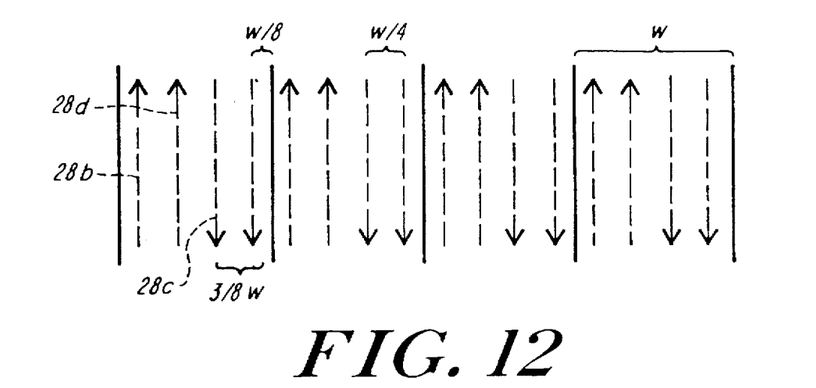
FIG. 12 is a schematic diagram illustrating ray placement as a result of the preferred method of the present invention.

For ease of illustration assuming the disk rotates 760° during a two revolution scan, FIG. 12 shows the ray placement of four positions of the disk 46: 180° and 360° of the first revolution when data is acquired, and those same positions of the disk (540° and 720°) during the second revolution of the two revolution scan. Assuming the detector offset is one-eighth of a detector-spacing (w/8) for the first 360° rotation, and three-eighths of a detector-spacing (3w/8) for the second 360° rotation, the arrows 28a, 28b, 28c and 28d indicate the center line of the ray corresponding to the 0° (720°), 180°, 360° and 540° positions of disk when projection views are taken, so that the rays provided during the second 360° revolution are interleaved with the rays provided during the first 360° revolution. The ray placements from the two revolutions are thus spaced apart by one-quarter of a detector-spacing (w/4), doubling the number of unique ray paths provided by the one-quarter of a detector offset of the prior art. Such a shift can be readily made without significantly slowing the rotation cycle if, for example, adjusting screw 112 is driven by stepping motor 66 as shown in FIG. 2. Such an arrangement, for example, can provide the shift in about 0.2 sec, so that where one revolution takes approximately 2 seconds, the disk 46 rotates approximately ⅒th of a revolution (36°) during the shift before data is again acquired during a second revolution. Alternatively, spine 60 can be driven between the two positions by an electrical solenoid.

It should be appreciated that since the detector system is movable between a one-eighth detector (w/8) offset and three-eighths detector (3w/8) offset by operating the stepping motor 66 in one mode of operation to achieve spacings between ray paths equal and opposite to one another of one-quarter of a detector-spacing (w/4), the system can be operated in a second mode of operation wherein the detector array is preset with a fixed one-quarter of a detector-spacing offset (w/4) prior to scanning by operating the stepping motor 66 to move the detector to that position.

The mounting system of the invention, therefore, provides the very fine adjustment needed for simplified setup and movement between scans and during a scan, as well as the ruggedness needed for rapid acceleration and deceleration. Because the mounting system of the invention meets these needs so well, it may be used in a novel manner according to the method of the invention to greatly improve the quality of the image by creating additional unique ray paths during a scan. Specifically, if the detector array is rapidly and accurately shifted a judicious amount at a precise position of the disk, as the disk rotates during a scan, a completely new set of ray paths can be provided so as to greatly enhance the quality of the image. It should also be appreciated that the system can work in other modes, and/or be constructed to provide detector shifts with other spacings relative to the center ray which might require additional whole or partial revolutions of a multiple scan, or may be accomplished all within a single 360° revolution of the disk. For example, shifts of w/8 and 7w/8 of a detector-spacing, or 3w/8 and 5w/8 of a detector-spacing would work equally well with a two revolution multiple scan. In a similar manner a four revolution multiple scan could employ detector positions w/16, 3w/16, 5w/16 and 7w/16, 9w/16, 11w/16, 13w/16 and 15w/16 of a detector-spacing relative to the center ray during the respective four revolutions of the four revolution multiple scan, wherein a shift occurs after each 360° rotation of the disk during the scan.

Figure 13:
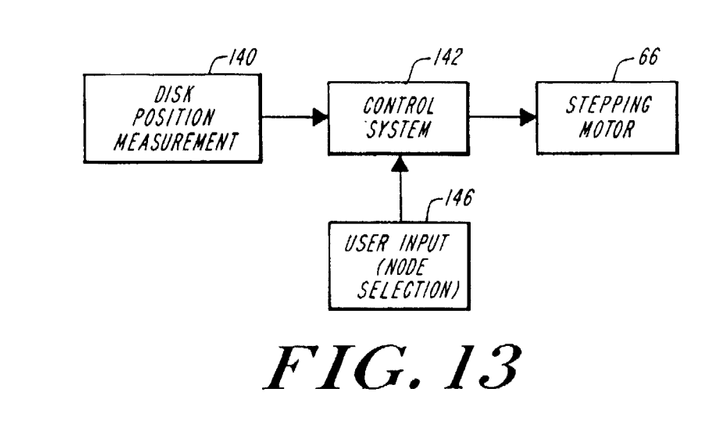
FIG. 13 is a block diagram of the detector array motion control system.

FIG. 13 shows a block diagram of the control system for accomplishing the offset shift in accordance with the principles of the present invention. As shown, position measurement system 140 is provided for sensing the angular position of the source 42 and detector array 44 so that the shifters of the detectors can be synchronized with the rotation of the disk 46. Position measurement system 140 is used to time the detector array shift at the prescribed 360° rotation of the two revolution scan and can be any device for determining angular position of a rotating object at the prescribed positions where shifts are to occur. For example, a cam secured to rotate with disk 46 can operate a micro-switch, or a magnet mounted on the disk can induce a trigger signal in a stationary pickup, at a precise angle of the source and detector array. In a preferred method, a shaft encoder of the type including indicia on the circumference of the disk is detected by a sensor arrangement and serves to time both the periodic sampling of the detectors and the shifting of the detector array. The preferred position measurement system is described in co-pending U.S. patent application Ser. No. 08/162,653; entitled Apparatus for and Method of Measuring Geometric, Positional and Kinematic Parameters of a Rotating Device; filed Dec. 6, 1993, in the names of Bernard M. Gordon, David Winston, Paul Wagoner and Douglas Abraham; and assigned to the present assignee, the application disclosure being herein incorporated. The output of position measurement means is connected to the control system 142 which is adapted to provide an output shift signal to control the stepping motor 66. The output is capable of controlling the reversible stepping motor one step at a time in either direction so that the number of steps required to move the detector array among the three positions of interest, e.g., one-eighth and three-eighths detector shift for the detector shift mode of operation, and one-quarter detector shift for the one-quarter detector shift offset mode of operation. A user input 146 can be provided to control 142 for selecting the mode of operation. Thus, the control will initially set the position of the detector array during each mode of operation; and, during the mode of operation requiring a shift of the detectors following the first 360° rotation of the two revolution scan, the control will provide a signal to the stepping motor so as to step the motor a sufficient amount so that the detector array shifts between the one-eighth and three-eighths of a detector-spacing. The control system has the added advantage that the user input indicated at 146 can be an easily accessible device, such as a keyboard, so that the detector array positions can be set and changed at any time without the necessity of taking the CAT scan system apart. Thus, precise detector placement is easily adjustable, making it easier to ship the tomography system, set the system up during installation and calibrate the detector placement as necessary on an on-going basis.

We have thus described a system and method of making tomographic images that provide better quality images by creating additional ray paths during a tomographic scan so that the additional data can be interleaved with other data. Combining fast multiple scans with ray path shifting reduces the effects of motion artifacts on tomography imaging without increasing the X-ray exposure to a patient during a scan. Such a combination provides an improved X-ray tomographic scan having the benefit of a longer scan from the point of view of quantum statistics without actually increasing the scanning time, nor the X-ray exposure level, as well as allowing the scan to be accomplished where the power source available is insufficient to deliver high rates of power. Increasing the number of additional ray paths by moving the detectors during the scan improves the image quality of a reconstructed image provided by a CAT scan system of the type having an array of detectors offset by a fixed quarter of the spacing of each detector. The improved mounting system for supporting the array of detectors provides precise detector placement relative to the X-ray source and isocenter and is sufficiently rugged to sustain high angular acceleration forces, and yet is adapted to rotate the detector array at least through a small angle about the focal spot between at least two precisely defined positions. The mounting system also facilitates and allows for easy adjustment of detector placement through an input device, such as a keyboard, making it easier to ship the tomography system, set the system up during installation and calibrate the detector placement as necessary on an on-going basis. The detector shift mounting system moves the detector array so that the tomographic system is capable of operation in either of at least two modes for defining scans for two different quality images.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. A tomography apparatus comprising:
    (a) tomographic scanning means including (i) an X-ray source including a focal spot from which X-rays are emitted, and (ii) X-ray detection means, including a plurality of detectors aligned with the focal spot within a scanning plane, for detecting X-rays emitted by said X-ray source along predetermined and unique ray paths extending along the scanning plane between the focal spot and corresponding ones of said detectors for each view of a tomographic scan so as to acquire image data as a function of the detected X-rays and the corresponding ray paths;
    (b) means for rotating at least the X-ray source in the scanning plane about a rotation axis so as to perform a tomographic scan for which image data is acquired; and
    (c) means for shifting the focal spot and detectors relative to one another between first and second relative positions so that
        (i) in said first relative position the detectors are offset relative to a line extending in the scanning plane from the focal spot through the rotation axis and one of the detectors such that the unique ray paths during a first 180° portion of a 360° rotation of the tomographic scanning means are different from the ray paths during a second 180° portion of a 360° rotation of the tomographic scanning means and
        (ii) in said second relative position the detectors are offset relative to said line extending in the scanning plane from the focal spot through the rotation axis and the one detector so that the unique ray paths during a 360° rotation of said tomographic scanning means are different from the ray paths provided during rotation of the tomographic scanning means with said source and detectors positioned in said first relative position so as to increase the number of unique ray paths during a tomographic scan.

2. A tomography apparatus according to claim 1, wherein the rotation axis intersects the scanning plane at a rotation center of the plane, and the means for rotating includes means for rotating the X-ray detection means with the X-ray source about the rotation axis, the apparatus further including:

sensing means for sensing the angular position of the tomographic scanning means about the rotation center;
    wherein the means for shifting the focal spot and detectors relative to one another includes moving means, responsive to the sensing means when the tomographic scanning means is at one or more predetermined angular positions, for moving the detectors relative to the focal spot between said first and second relative positions so as to approximate rotational movement of said detectors about said focal spot.

3. A tomographic apparatus according to claim 2, wherein said means for rotating the X-ray detection means with the X-ray source about the rotation axis includes means for rotating the detection means and source through at least two successive 360° revolutions during which image data is acquired, the sensing means including means for sensing the ending of said first 360° revolution and said moving means being responsive to the sensing means when said sensing means senses the ending of said first 360° revolution so that the detectors are positioned in one of said first and second relative positions during the first 360° revolution and said moving means moves the detectors from said one of said first and second positions to the other of said first and second positions prior to the second 360° revolution.

4. A tomography apparatus according to claim 3, further including means for summing the image data acquired during each revolution to the image data acquired to each of the other revolutions of the tomographic scan.

5. A tomography apparatus of the type comprising: (a) tomographic scanning means including (i) an X-ray source having a focal spot and (ii) X-ray detection means, including a plurality of detectors aligned with said source within a scanning plane, for detecting X-rays emitted by said X-ray source; and (b) means for rotating said tomographic scanning means in a scanning plane about a rotation axis so as to define a center of rotation within the scanning plane and so as to generate image data during a tomographic scan for producing a tomographic scanned image; the improvement comprising:

moving means for moving said X-ray detection means relative to a center line extending from the focal spot through the center of rotation during said scan between at least a first position wherein the center line intersects one of said plurality of detectors at a point that is spaced apart from the center of said one detector by a first spacing, and a second position different from said first position wherein the center line intersects said one detector at a point that is spaced apart from the center of said one detector by a second spacing different from said first spacing so that image data generated during a tomographic scan with the detection means in said first position is different from and complements the image data generated during a tomographic scan with the detection means in the second position so as to improve the quality of the tomographic scanned image.

6. Apparatus according to claim 5, wherein said moving means includes means synchronized with the rotation of said tomographic scanning means so that the X-ray detection means shifts from said first position to said second position during said tomography scan.

7. Apparatus according to claim 6, wherein the first spacing of said first position of said X-ray detection means defines a n/8 of a detector-spacing offset, and the second spacing of said second position of said X-ray detection means defines a n/8+¼ of a detector-spacing offset, wherein n is an odd integer 1, 3, 5 or 7.

8. Apparatus according to claim 5, wherein said means for rotating said tomographic scanning means includes means for rotating said tomographic scanning means through at least two revolutions about the rotation axis during a scan so that data is acquired during each of said revolutions, said moving means positioning said detection means in said first position during the first revolution of said scan, and in the second position during the second revolution of said scan.

9. Apparatus according to claim 5, wherein said moving means is operable in at least two modes, wherein in a first of said modes said moving means moves said detection means from the first position to the second position during the tomographic scan, and in the second of said modes said moving means moves the detection means to a third position, different from said first and second positions, prior to said scan and maintains the detection means at said third position throughout said scan.

10. Apparatus according to claim 9, wherein in said first position of said X-ray detection means of said first mode said first spacing defines a n/8 of a detector-spacing offset, and in the second position of said X-ray detection means of said first mode said second spacing defines a n/8+¼ of a detector-spacing offset, wherein n is an odd integer 1, 3, 5 or 7, and said moving means includes means synchronized with the rotation of said scanning means so that the X-ray detection means shifts at a predetermined position of said tomography scan means during said tomography scan; and said third position of said second mode defines a one-fourth of a detector-spacing offset between said center line and the center of said one detector.

11. Apparatus according to claim 5, wherein said X-ray detection means includes an array of detectors, said apparatus further including means for mounting said array on an arc of a circle having a center of curvature substantially coincident with said focal spot, wherein said moving means includes means for moving said array between said first and second positions so that said array remains on said arc of said circle in each of said positions.

12. Apparatus according to claim 11, wherein said moving means includes a suspension system for supporting said array so that said array is constrained to move as though it were pivoting about said focal spot.

13. A tomography apparatus of the type comprising: (a) tomographic scanning means including (i) an X-ray source having a focal spot and (ii) X-ray detection means, including a plurality of detectors aligned with said source within a scanning plane, for detecting X-rays emitted by said X-ray source; and (b) means for rotating said tomographic scanning means in a scanning plane about a rotation axis so as to define a center of rotation within the scanning plane and so as to generate image data during a tomographic scan for producing a tomographic scanned image; the improvement comprising:

moving means for moving said X-ray detection means relative to a center line extending from the focal spot through the center of rotation during said scan between at least a first position wherein the center line intersects one of said plurality of detectors at a point that is spaced apart from the center of said one detector by a first spacing, and a second position different from said first position wherein the center line intersects said one detector at a point that is spaced apart from the center of said one detector by a second spacing so that image data generated during a tomographic scan with the detection means in said first position is different from and complements the image data generated during a tomographic scan with the detection means in the second position so as to improve the quality of the tomographic scanned image, wherein said X-ray detection means includes an array of detectors, said apparatus further including means for mounting said array on an arc of a circle having a center of curvature substantially coincident with said focal spot, wherein said moving means includes means for moving said array between and first and second positions so that said array remains on said arc of said circle in each of said positions, wherein said moving means includes a suspension system for supporting said array so that said array is constrained to move as though it were pivoting about said focal spot, wherein said suspension system includes a four bar suspension system comprising two links substantially aligned with said center of curvature in each of said positions, for supporting said array on said tomographic scanning means, and means for moving said array so that said array pivots on said links so as to approximate rotational motion about the focal spot.

14. Apparatus according to claim 13, further including source and detector support means for supporting said X-ray source and said X-ray detection means and rotatable about said axis, and array support means for supporting said array, and wherein said links each includes a flexible plate having one end connected to said source means and its opposite end connected to said array support means.

15. Apparatus according to claim 14, wherein each of said links further includes stiffening means secured to said flexible plate so as to define the four pivot points of the four bar suspension system.

16. Apparatus according to claim 14, wherein said array support means is an arcuate spine member.

17. Apparatus according to claim 14, wherein said moving means includes a motor and drive means, coupled to the motor and said array support means, so that operation of said motor in one direction moves said array support means in a direction from said first position to the second position, and operation of said stepping motor in the other direction moves said array support means in a direction from said second position to the first position.

18. Apparatus according to claim 14, further including means for biasing each of said links so that the array support remains at a substantially fixed distance from said X-ray source at said first and second positions.

19. In a tomography system having a radiation source defining a focal spot, an array of detectors, and disk means for supporting said source and array for rotation about a central axis such that a center line extends through the focal spot and the central axis, said system further comprising:

a mounting system for attaching said array of detectors to said disk said mounting system comprising:
(a) a base for supporting said array
(b) a suspension system for suspending said base relative to said disk; and
(c) means for varying the angular location of said detector array between a first position and a second position with respect to said source and said center line, the first position being such that when said array of detectors is in the first position the center line intersects one of said detectors at a point that is spaced apart from the center of said one detector by a first spacing, and the second position being such that when said array of detectors is in the second position the center line intersects said one detector at a point that is spaced apart from the center of said one detector by a second spacing different from said first spacing, wherein said suspension system comprises first and second link supports, each for coupling said base to said disk means so as to form a four bar suspension system, said link supports each comprising hinge means for permitting the movement of said base so as to approximate rotational movement of said base about said focal spot between said first and second positions.

20. A mounting system as in claim 19, wherein said detectors of said array subtend an equal angle relative to said focal spot at each of said first and second positions.

21. A mounting system as is in claim 20, wherein said first and second positions are separated by one quarter of the detector-spacing.

22. A mounting system as in claim 19, wherein each of said link supports comprises a flexible plate.

23. A mounting system as in claim 22, wherein each of said link supports further comprise stiffening means for limiting the flexing of each of said flexible plates to two narrow parallel areas, wherein said hinge means are defined by each of said areas.

24. A mounting system as in claim 23, wherein said flexible plates lie approximately in respective planes that intersect at said focal spot.

25. A mounting system as in claim 22, further including means for tensioning said base so as to maintain the distance of said array from said focal spot constant.

26. A mounting system as in claim 19, wherein said means for varying the angular location of said detector array between said first and second positions comprises automatic shifting means for automatically shifting said detector array between said first and second positions during a scan.

27. A mounting system as in claim 26, wherein said automatic shifting means comprises reversible motor means, responsive to a shifting signal, means for coupling said motor means to said base so that operation of said motor means moves said array between said first and second positions, and means for generating said shifting signal as a function of the position of said disk means.

28. A method of scanning an object with a scanning tomography system of the type having a radiation source defining a focal spot, an array of uniformly spaced radiation detectors arranged in an arc having a center of curvature substantially coincident with said focal spot so as to subtend an equal angle about said focal spot, means for rotating said source and array about a rotation axis; means for taking periodic output measurements from said detectors during rotation, and means for using said output measurements to generate a density image of said object; said method comprising the steps of:

a. Conducting a first 360° scanning rotation cycle with the detector array positioned in a first position relative to a center line passing through the focal spot and the central axis, wherein the center line intersects one of the detectors at a first point spaced apart from the center of said one detector by a first spacing to obtain a first set of detector output measurements;

b. Shifting the detector array, relative to said center line, from the first position to a second position wherein the center line intersects said one detector at a second point spaced apart from the center of said one detector by a second spacing different from the first spacing;

c. Conducting a second 360° scanning rotation cycle to obtain a second set of detector output measurements different from said first set; and d. Using both sets of detector output measurements to generate a single density image.

29. A method as in claim 28, wherein said step of shifting said detector array includes the step of shifting the detector array one-fourth the spacing of a detector.

30. A method as in claim 28, wherein steps a, b and c are conducted without interrupting the scanning rotation.

31. A method as in claim 28, wherein one of said first and second spacings is substantially equal to one-eighth of the detector-spacing.

32. A tomography apparatus comprising:
(a) tomographic scanning means including (i) an X-ray source including means for defining a focal spot from which X-rays emanate, and (ii) X-ray detection means, including a plurality of detectors aligned with the X-ray source within a scanning plane, for detecting X-rays emitted by said focal spot along predetermined and unique ray paths extending along the scanning plane between the focal spot and corresponding ones of said detectors for each view of a tomographic scan so as to acquire image data of a scanned image as a function of the detected X-rays and the corresponding ray paths;
(b) means for rotating at least the X-ray source in the scanning plane about a rotation axis extending through said scanning plane at an isocenter so as to perform a tomographic scan for which image data is acquired; and
(c) means for shifting the focal spot and detectors relative to one another so as to acquire at least three different sets of interleaved image data during a tomographic scan for use in reconstructing said scanned image.

33. A tomography apparatus according to claim 32, wherein said means for shifting the focal spot and detectors relative to one another shifts said focal spot and detectors relative to one another so as to acquire at least four different sets of interleaved image data during a tomographic scan for use in reconstructing said scanned image.

34. A tomography apparatus according to claim 32, wherein said means for shifting the focal spot and detectors relative to one another moves said focal spot and detectors relative to one another between first and second relative positions.

35. A tomography apparatus according to claim 34, wherein said first position is defined by a center line drawn from the focal spot through the isocenter to one of said detectors such that the center line intersects the one detector at a location offset from its center by $n/8$ of a detector-spacing, and the second position is defined by a center line drawn from the focal spot through the isocenter to said one detector such that said center line intersects the one detector at a location offset from its center by $n/8 \pm \frac{1}{4}$ of a detector-spacing, wherein n is an odd integer 1, 3, 5 or 7.

* * * * *

UNITED STATES PATENT AND TRADEMARK OFFICE
CERTIFICATE OF CORRECTION

PATENT NO.: 5,768,331

DATED: June 16, 1998

INVENTOR(S): Bernard M. Gordon et al.

It is certified that error appears in the above-identified patent and that said Letters Patent is hereby corrected as shown below:

Claim 7, column 13, line 61, delete "$n/8+¼$", and insert therefor -- $n/8±¼$ --.

Claim 10, column 14, line 17, delete "$n/8+¼$", and insert therefor -- $n/8±¼$ --.

Signed and Sealed this

First Day of September, 1998

*Attest:*

BRUCE LEHMAN

*Attesting Officer*          Commissioner of Patents and Trademarks